United States Patent
Blenke et al.

[11] Patent Number: 6,129,720
[45] Date of Patent: Oct. 10, 2000

[54] EXTENSIBLE ABSORBENT ARTICLE INCLUDING AN EXTENSIBLE ABSORBENT PAD LAYER

[75] Inventors: Timothy James Blenke, Neenah; Jennifer Elizabeth Pozniak, Appleton; Richard Warren Tanzer, Neenah, all of Wis.; Hugh Michael Sexton, Newman, Ga.

[73] Assignee: Kimberly-Clark Worldwide, Inc., Neenah, Wis.

[21] Appl. No.: 09/002,077

[22] Filed: Dec. 31, 1997

[51] Int. Cl.⁷ ...................................... A61F 13/15
[52] U.S. Cl. ................... 604/385.16; 604/358; 604/367; 604/385.01; 604/385.22; 604/385.24; 604/385.27
[58] Field of Search ................................ 604/368, 385.2, 604/369, 373, 367, 378, 385.16, 358, 385.27, 385.24, 385.01, 385.22

[56] References Cited

U.S. PATENT DOCUMENTS

| | | |
|---|---|---|
| H1420 | 2/1995 | Richardson ........................... 604/385.2 |
| H1558 | 7/1996 | Goulait et al. ........................... 156/210 |
| 1,246,910 | 9/1917 | Liloia et al. . |
| 1,950,765 | 3/1934 | Winter ........................................ 223/15 |
| 2,073,329 | 3/1937 | Winter ........................................ 154/33 |
| 2,866,459 | 12/1958 | Soelson ..................................... 128/284 |
| 3,058,169 | 10/1962 | Joa ......................................... 19/144.5 |
| 4,051,854 | 10/1977 | Aaron ....................................... 128/284 |
| 4,573,987 | 3/1986 | Lamb, Jr. .................................. 604/378 |
| 4,574,024 | 3/1986 | VanMalderer ............................. 156/202 |
| 4,655,760 | 4/1987 | Morman et al. ..................... 604/385 A |
| 4,657,802 | 4/1987 | Morman ................................... 428/152 |
| 4,699,620 | 10/1987 | Bernardin ........................... 604/385 A |
| 4,701,114 | 10/1987 | Wilson et al. ...................... 604/385 A |
| 4,701,170 | 10/1987 | Wilson et al. ...................... 604/385 A |
| 4,701,171 | 10/1987 | Boland et al. ....................... 604/385 A |
| 4,701,172 | 10/1987 | Stevens .............................. 604/385 A |
| 4,701,173 | 10/1987 | Zehner et al. ...................... 604/385 A |
| 4,701,174 | 10/1987 | Johnson .............................. 604/385 A |
| 4,701,176 | 10/1987 | Wilson et al. ...................... 604/385 A |
| 4,704,116 | 11/1987 | Enloe . |
| 4,747,846 | 5/1988 | Boland et al. ....................... 604/38 A |
| 4,756,709 | 7/1988 | Stevens .............................. 604/385 A |
| 4,770,656 | 9/1988 | Proxmire et al. ....................... 694/393 |
| 4,781,962 | 11/1988 | Zamarripa et al. .................... 428/138 |
| 4,808,176 | 2/1989 | Kielpikowski ...................... 604/385.2 |

(List continued on next page.)

FOREIGN PATENT DOCUMENTS

| | | |
|---|---|---|
| 1316651 | 4/1993 | Canada .................................. 128/287 |
| 0 412 549 A1 | 2/1991 | European Pat. Off. . |
| 0 819 414 A2 | 1/1998 | European Pat. Off. . |
| WO 93/01785 A1 | 2/1993 | WIPO . |
| WO 94/02095 A1 | 2/1994 | WIPO . |
| WO 97/47264 A1 | 12/1997 | WIPO . |

*Primary Examiner*—John G. Weiss
*Assistant Examiner*—Miley Craig Peppers, II
*Attorney, Agent, or Firm*—Thomas D. Wilhelm

[57] ABSTRACT

An absorbent article includes an absorbent pad and an outer cover. An extensible layer replaces at least one of the tissue layers of the absorbent pad. The extensible layer can be secured to an extensible bodyside liner or an extensible outer cover. The extensible layer is adhesively secured to the inner surface of the outer cover or the bodyside liner. In embodiments where the outer cover is extensible in a cross-direction and/or a longitudinal direction, the extensible layer is extensible in the same directions and moves with the outer cover. Absorbent core is not physically secured to the extensible layer. Thus the extensible layer has free mobility with respect to the absorbent core when the outer cover is extended, without deleterious effect on the absorbent core, or the absorbent pad as a whole. Therefore, tearing of the absorbent pad and damage to, or release, of superabsorbent material from the absorbent pad is prevented. In some embodiments, the adhesive securing elements can comprise an elastic adhesive material.

32 Claims, 5 Drawing Sheets

U.S. PATENT DOCUMENTS

| | | | |
|---|---|---|---|
| 4,834,736 | 5/1989 | Boland et al. | 604/385.2 |
| 4,834,738 | 5/1989 | Kielpikowski et al. | 604/385.2 |
| 4,834,742 | 5/1989 | Wilson et al. | 604/389 |
| 4,838,885 | 6/1989 | Bernardin | 604/385.1 |
| 4,842,596 | 6/1989 | Kielpikowski et al. | 604/385.2 |
| 4,846,825 | 7/1989 | Enloe et al. | 604/385.1 |
| 4,847,134 | 7/1989 | Fahrenkrug et al. | 428/138 |
| 4,850,990 | 7/1989 | Huntoon et al. | 604/385.2 |
| 4,872,871 | 10/1989 | Proxmire et al. | 604/394 |
| 4,892,535 | 1/1990 | Bjornberg et al. | 604/380 |
| 4,895,569 | 1/1990 | Wilson et al. | 604/386 |
| 4,936,840 | 6/1990 | Proxmire | 604/385.2 |
| 4,965,122 | 10/1990 | Morman | 428/228 |
| 5,019,066 | 5/1991 | Freeland et al. | 604/385.2 |
| 5,171,239 | 12/1992 | Igaue et al. . | |
| 5,226,992 | 7/1993 | Morman . | |
| 5,246,433 | 9/1993 | Hasse et al. | 604/396 |
| 5,246,772 | 9/1993 | Manning | 156/164 |
| 5,316,601 | 5/1994 | Hebbard et al. | 156/62.2 |
| 5,376,198 | 12/1994 | Fahrenkrug et al. | 156/164 |
| 5,393,599 | 2/1995 | Quantrille et al. | 428/284 |
| 5,411,497 | 5/1995 | Tanzer et al. | 604/368 |
| 5,425,725 | 6/1995 | Tanzer et al. | 604/368 |
| 5,433,715 | 7/1995 | Tanzer et al. | 604/368 |
| 5,440,764 | 8/1995 | Maatsushita | 2/401 |
| 5,458,592 | 10/1995 | Abuto et al. | 604/378 |
| 5,464,401 | 11/1995 | Hasse et al. | 604/385.1 |
| 5,470,639 | 11/1995 | Gessner et al. | 428/152 |
| 5,476,711 | 12/1995 | Hebbard et al. | 428/283 |
| 5,486,166 | 1/1996 | Bishop et al. . | |
| 5,490,846 | 2/1996 | Ellis et al. . | |
| 5,496,429 | 3/1996 | Hasse et al. | 156/73.3 |
| 5,518,801 | 5/1996 | Chappell et al. | 428/152 |
| 5,531,732 | 7/1996 | Wood | 604/391 |
| 5,543,206 | 8/1996 | Austin et al. | 428/198 |
| 5,582,606 | 12/1996 | Bruemmer et al. . | |
| 5,593,399 | 1/1997 | Tanzer et al. | 604/368 |
| 5,658,269 | 8/1997 | Oshborn, III et al. | 604/385.2 |
| 5,702,378 | 12/1997 | Widlund et al. | 604/373 |
| 5,800,419 | 9/1998 | Soga et al. | 604/368 |
| 5,824,004 | 10/1998 | Osborn, III et al. | 604/385.2 |
| 5,827,259 | 10/1998 | Laux et al. | 604/385.2 |
| 5,833,677 | 11/1998 | Sauer | 604/369 |
| 5,843,056 | 12/1998 | Good et al. | 604/367 |

EXTENSIBLE ABSORBENT ARTICLE INCLUDING AN EXTENSIBLE ABSORBENT PAD LAYER

CROSS REFERENCE TO RELATED APPLICATIONS

Not Applicable

STATEMENT REGARDING FEDERALLY SPONSORED RESEARCH OR DEVELOPMENT

Not Applicable

FIELD OF THE INVENTION

Absorbent articles such as infant diapers, training pants, adult incontinence products, and the like are well known. Such absorbent articles have achieved wide acceptance due to their ability to receive and absorb body exudates, whether large amounts or small, and generally include an absorbent core therein.

In typical absorbent articles, an absorbent pad has an absorbent core contained within a barrier tissue and a forming tissue. The absorbent pad is located between an outer cover and a bodyside liner.

This invention pertains to extensible absorbent articles for use in receiving and storing exudates. The outer cover generally comprises a material extensible in at least one direction. An adhesive is generally applied to a first inner surface of the outer cover. The adhesive generally secures the outer cover to the absorbent pad, such as a barrier or forming tissue of the absorbent pad. The forming tissue is secured in surface-to-surface relationship to the barrier tissue about the perimeter of an absorbent core.

BACKGROUND OF THE INVENTION

In general, absorbent articles should comfortably fit the body of a wearer. Most absorbent articles include an absorbent pad formed by an absorbent core contained in a wrap comprising a barrier tissue and/or a forming tissue. The subject invention discloses an absorbent article generally having extensibility in at least one direction, preferably the cross-direction. Such extensibility permits an absorbent article to extend and expand about the wearer and thus to better conform to the body of the wearer. Such extension and expansion about the wearer is feasible because both the bodyside liner and the outer cover are extensible in at least the one direction.

In conventional structures, the outer cover is typically adhesively secured to the forming tissue of the absorbent pad. In such embodiments, extending the outer cover in the cross-direction extends the forming tissue in the cross-direction. The force used to extend the outer cover, and thence the absorbent pad, can tear or otherwise damage the forming tissue or the barrier tissue of the absorbent pad. Since the absorbent pad is typically a sealed enclosure, namely an absorbent core enclosed within the combination of a forming tissue and a barrier tissue, tearing the absorbent pad, namely either the forming tissue or the barrier tissue, can release superabsorbent particles and other absorbent materials, such as cellulose fluff into contact with the body of the wearer. Superabsorbent particles can irritate the skin of the wearer. Such tearing of the absorbent pad indicates failure of the absorbent article to perform properly. Therefore, it is critical to find a way to prevent tearing or other structural failure of the absorbent pad.

SUMMARY OF THE DISCLOSURE

In the present invention, an absorbent article includes an absorbent core having a first side and a second side, an extensible layer of material having a first surface disposed adjacent the first side of the absorbent core, and a second opposing surface, an extensible outer cover having a third outer cover surface and a fourth opposing outer cover surface, the second surface of the extensible layer being disposed in surface-to-surface relationship with the third outer cover surface: and a pattern of adhesive between the extensible layer and the outer cover, the pattern of adhesive adhesively mounting the extensible layer to the outer cover such that extension of the outer cover can extend the extensible layer, the absorbent core being relatively free to move over the first surface of the extensible layer, thus sections of the absorbent core are free to move, within the absorbent article, with respect to the outer cover.

In some embodiments, the absorbent core has complete freedom of movement over the first surface of the extensible layer, thus to move, within the absorbent article, with respect to the outer cover.

In other embodiments, the absorbent core is adhesively bonded to a first surface of the extensible layer, along a center line, either across or along the length of the absorbent article. In this manner, the absorbent core is held in place relative to the extensible layer along the center line.

In many embodiments, the extensible layer comprises a layer of extensible spunbonded material.

In some embodiments, the absorbent article includes a tissue disposed adjacent the second side of the absorbent core. The tissue and the extensible layer, in combination, contain the absorbent core and thus comprise an absorbent pad.

In some embodiments, the tissue and the extensible layer are secured to each other about at least a portion of an outer perimeter of the absorbent core.

In many embodiments, a bodyside liner is disposed in surface-to-surface relationship with the tissue.

In some embodiments, at least one of the bodyside liner and the outer cover comprise a resiliently extensible material.

In other embodiments, the absorbent core is adhesively bonded to a surface of the tissue adjacent the bodyside liner, along a center line, either across or along the length of the absorbent article. In this manner, the absorbent core is held in place, relative to the tissue, along the center line.

In some embodiments, the bodyside liner and the outer cover both are resiliently extensible, and have substantial extensibility in each direction.

In preferred embodiments, the bodyside liner and the outer cover are both extensible in at least the cross-direction.

In some embodiments, the absorbent core, the extensible layer, and the tissue, in combination, comprise an absorbent pad. The absorbent pad has an outer perimeter. A pattern of adhesive is disposed on the outer cover outwardly of the absorbent pad such that the outwardly disposed adhesive secures the outer cover to the bodyside liner at locations disposed outwardly of the outer perimeter of the absorbent pad.

In some embodiments, the outer cover comprises a neck bonded laminate.

In some embodiments, the absorbent article includes first and second containment flaps.

In some embodiments, the absorbent article is devoid of separate waist elastic elements.

In some embodiments, the absorbent article includes leg elastics disposed at least in the crotch portion to provide extensibility and retraction in the longitudinal direction.

In some embodiments, the pattern of adhesive comprises a plurality of swirl patterns.

In some embodiments, the adhesive comprises elastic adhesive material.

Another absorbent article of the present invention comprises an extensible outer cover, and a bodyside liner mounted in surface-to-surface relationship to at least a portion of a first inner surface of the outer cover, an absorbent pad disposed between the bodyside liner and the outer cover, comprising an absorbent core and including a first extensible layer of material disposed between the absorbent core and the outer cover, the absorbent pad including a second layer of material disposed between the absorbent core and the bodyside liner, and adhesive material disposed between the outer cover and the first extensible layer and mounting the outer cover and the first extensible layer to each other, such that extension of the outer cover can extend the extensible layer, the absorbent core having freedom of movement over the third surface of the first extensible layer, to move, within the absorbent article, with respect to the outer cover.

In some embodiments, the bodyside liner, the outer cover, and the extensible layer are extensible in at least the cross-direction, the first extensible layer enabling the outer cover to extend at least about 30 percent in the cross-direction without damaging the absorbent pad.

In other embodiments, the extensible layer enables the outer cover to extend at least about 200 percent in the cross-direction without damaging the absorbent pad.

In some embodiments, the extensible layer enables the outer cover to extend at least about 30 percent in the longitudinal direction without damaging the absorbent pad.

In some embodiments the first extensible layer and a second extensible layer are secured to each other about the absorbent core, thereby, in combination with the absorbent core, to form the absorbent pad.

In some embodiments, the first extensible layer and the second extensible layer have substantially equal extensibility in at least the cross-direction.

In some embodiments, the second extensible layer comprises an extensible material.

In some embodiments, the second extensible layer comprises a spunbond material.

Figure 1:
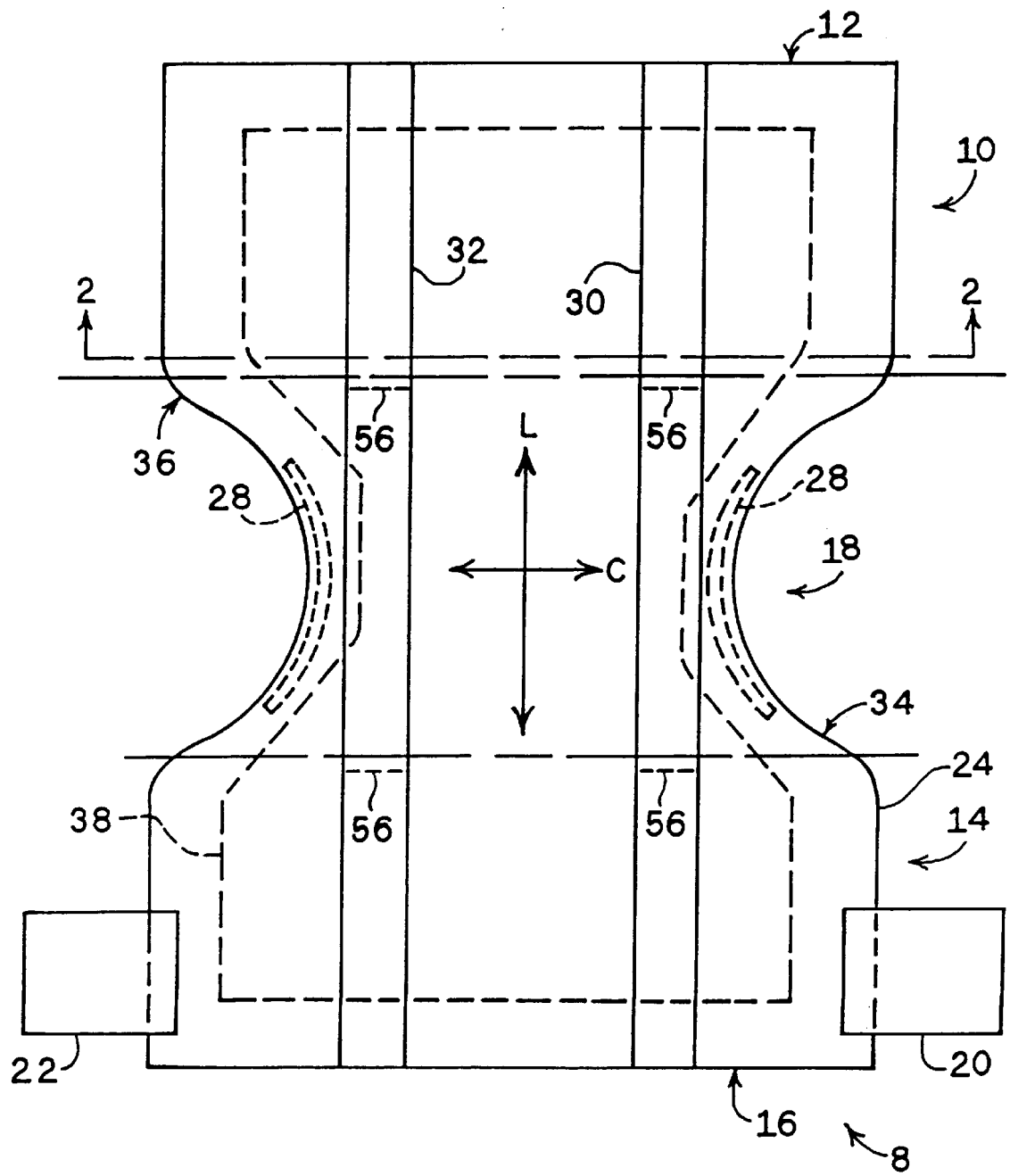
FIG. 1 shows a top view of a first embodiment of absorbent articles of the invention.

The invention is not limited in its application to the details of construction and the arrangements of components set forth in the following description or illustrated in the drawings. The invention is capable of other embodiments or of being practiced or carried out in various ways. Also, it is to be understood that the terminology and phraseology employed herein is for purpose of description and illustration and should not be regarded as limiting. Like reference numerals are used to indicate like components. The drawings are for purposes of illustration, and are not necessarily drawn to scale.

DETAILED DESCRIPTION OF THE ILLUSTRATED EMBODIMENTS

The various embodiments of the present invention will be described in relationship to their use in absorbent articles, but it should be understood that potential uses of the structures of the present invention need not be limited to the context of absorbent articles.

As used herein and in the claims that follow, the phrase "absorbent article" is meant to include diapers, training pants, adult incontinence articles, feminine hygiene products, and the like. Such articles generally receive and/or store urine and/or fecal material, or have a significant other absorbent function.

FIG. 1 is a representative plan view of an absorbent article 8 of one embodiment of the present invention, in its uncontracted state (i.e. with all elastic induced gathering and contraction removed). Absorbent article 8, shown in FIG. 1, includes a front portion 10 having a front edge 12, a rear portion 14 having a rear edge 16, and a crotch portion 18 between front portion 10 and rear portion 14. Fastening tabs 20, 22 are secured to bodyside liner 24 at opposing sides of rear portion 14 of absorbent article 8. Fastening tabs 20, 22 extend outwardly from the sides of rear portion 14. Outer cover 26 (shown in FIG. 2) lies in surface-to-surface relationship with bodyside liner 24 at outer edges of the outer cover and the bodyside liner. Leg elastics 28 provide generally longitudinal retractable extensibility and support in crotch portion 18. Containment flaps 30, 32 extend longitudinally along the length of absorbent article 8 inwardly of respective side edges 34. 36 of the absorbent article. Containment flaps 30, 32 are typically secured to bodyside liner 24. Absorbent pad 38 may have an hour-glass shape, and is disposed between bodyside liner 24 and outer cover 26.

Figure 2:
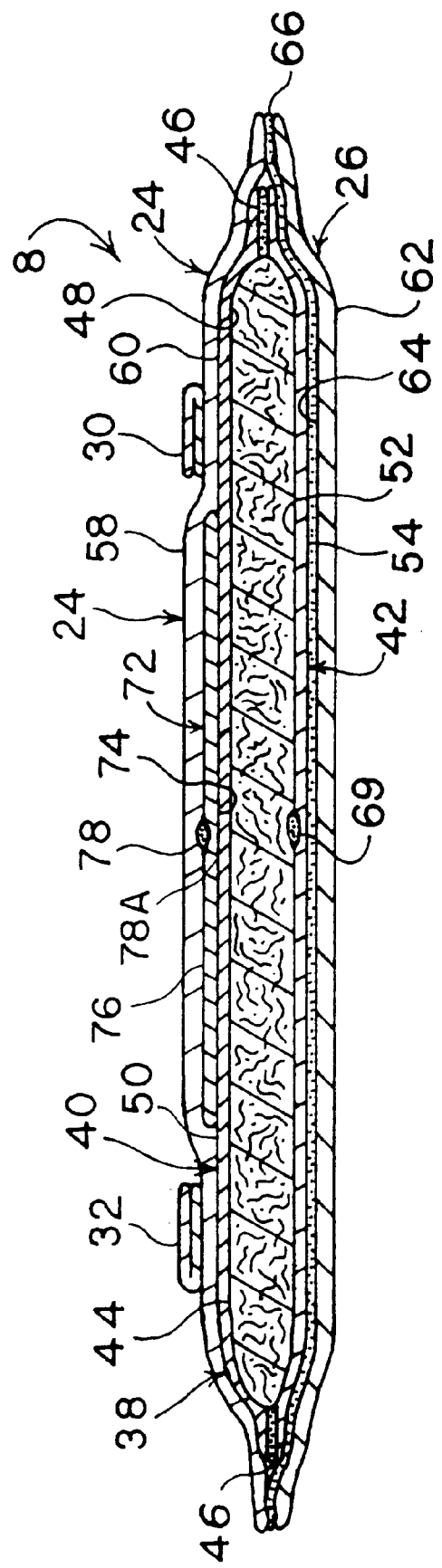
FIG. 2 shows a cross section view of the absorbent article taken at 2—2 of FIG. 1.

FIG. 2 illustrates a cross-section view taken at 2—2 of FIG. 1. Absorbent pad 38 is located between bodyside liner 24 and outer cover 26. Absorbent pad 38 includes a tissue 40. such as a barrier tissue, and an extensible layer 42 surrounding an absorbent core 44, the absorbent core having first and second sides. A layer/pattern of adhesive 46 is disposed between tissue 40 and extensible layer 42 about the respective outer perimeters thereof, and thus secures tissue 40 and extensible layer 42 to each other about the respective perimeters. Thus tissue 40 and extensible layer 42 enclose absorbent core 44 and, in combination with the absorbent core, form absorbent pad 38. Tissue 40 includes opposing surfaces 48 and 50. Extensible layer 42 includes inner surface 52 and opposing outer surface 54. Absorbent pad 38 receives and retains exudates that pass through bodyside liner 24. Adhesive pattern 46 secures surface 48 of tissue 40 to surface 52 of extensible layer 42 about an outer perimeter of absorbent core 44. Adhesive pattern 46 can be disposed over the entirety of any one or more of absorbent core 44, extensible layer 42, or tissue 40. A first side of absorbent core 44 is disposed adjacent surface 52 of extensible layer 42. Likewise a second side of absorbent core 44 is disposed adjacent surface 48 of tissue 40.

Bodyside liner 24 has opposing surfaces 58 and 60. Surface 60 of bodyside liner 24 is disposed in surface-to-surface relationship with surface 50 of tissue 40.

Outer cover 26 includes outer surface 62 and opposing inner surface 64. A pattern of adhesive 66 secures a portion of inner surface 64 of outer cover 26 in surface-to-surface relationship with outer surface 54 of extensible layer 42. The pattern of adhesive 66 is disposed on inner surface 64 and also secures outer cover 26 to bodyside liner 24.

The pattern of adhesive 66 does not include a pattern covering the entirety of inner surface 64 of outer cover 26. Such an amount of adhesive over the entire surface would completely secure outer cover 26 to extensible layer 42 such that no significant extensibility or stretch would be present between the outer cover and the extensible layer. Therefore, it is critical that the pattern of adhesive 66 be at selected portions of inner surface 64. While the pattern of adhesive 66 can cover most of inner surface 64, the entirety of inner surface 64 cannot be covered with adhesive, for outer cover 26 and extensible layer 42 to extend and function properly.

Figure 3:
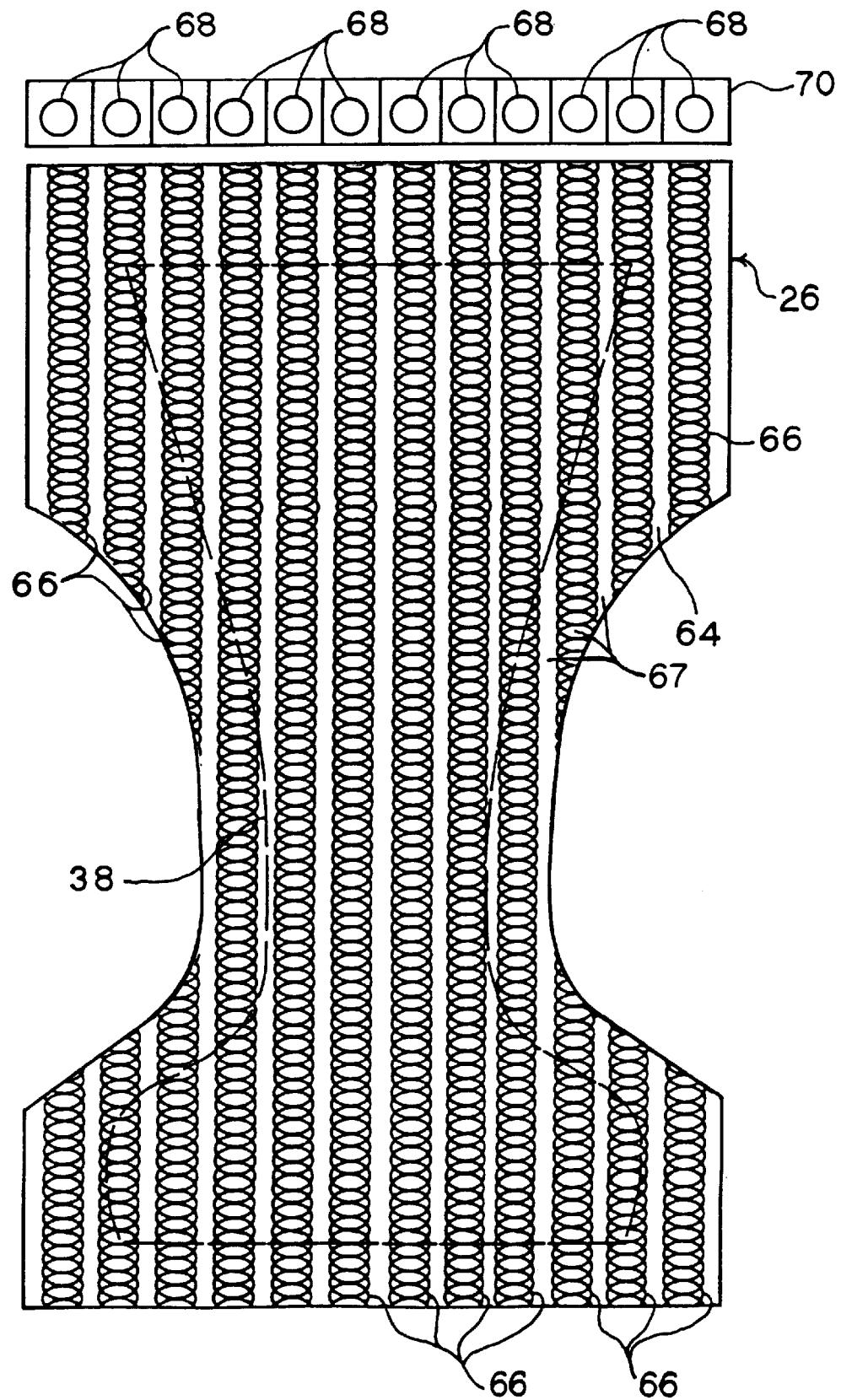
FIG. 3 shows an outer cover having adhesive applied thereto in a preferred adhesive pattern.

In preferred embodiments of the invention, outer cover 26 and bodyside liner 24 are both extensible, preferably both resiliently extensible, elements. Outer cover 26 preferably is extensible at least in cross-direction "C". If only outer cover 26 were extensible, and if the outer cover were secured to a respective non-extensible layer 42 over a substantial area of the facing surfaces of the two layers, the outer cover could apply sufficient force to the non-extensible layer to cause the non-extensible layer to tear, thus releasing superabsorbent material from the absorbent pad. Thus, where layer 42 is non-extensible, the securement between outer cover 26 and layer 42 can be no more than nominal.

Where outer cover 26 and layer 42 are mutually and equally extensible, any desired pattern 66 of adhesive can be used, including a pattern covering a large portion of the respective facing surfaces 54, 64.

Where outer cover 26 is more extensible than layer 42 in at least one direction, or when the outer cover has a lower stress/strain ratio than layer 42, adhesive pattern 66 can be designed to provide for greater stretching of outer cover 26 than of layer 42 in at least one direction. The adhesive-free spaces 67 in pattern of adhesive 66 shown in FIG. 3 provide for such differential stretching. Adhesive-free spaces 67 show areas where outer cover 26 is free to stretch without opposition from adhesive. Any adhesive pattern that provides such unbonded spaces or areas is a satisfactory adhesive pattern.

Stress/strain ratio is defined as the stress (force)/ strain (elongation). Thus a material having a stress/strain ratio of 2 grams/millimeter of elongation requires greater force to elongate one millimeter than a material having a stress/strain ratio of 1 gram/millimeter of elongation. Stress/strain ratio has no function or relevance in terms of the retractability of the material.

In preferred embodiments, the material used to make extensible layer 42, and thus layer 42 itself, is extensible in at least the same direction or directions as outer cover 26, and preferably extensible to at least the same extent as the outer cover and with at least the same or a smaller stress/strain ratio than the outer cover. Thus in normal use, extensible layer 42 is adhesively secured to outer cover 26, and can extend and thus follow the movement of the outer cover while effectively assisting tissue 40 in retaining absorbent core 44 in absorbent pad 38. Such extensibility of layer 42 enables the layer to not tear or break in response to extension of outer cover 26 and thus to assist tissue 40 in retaining absorbent core 44, and correspondingly the superabsorbent material, in the absorbent pad.

Absorbent core 44 is in general not physically secured to extensible layer 42 or to tissue 40. This general non-securement between extensible layer 42 and absorbent core 44 provides the absorbent core with protection from tearing during movement or extension, within absorbent article 8, of outer cover 26 and extensible layer 42.

In some embodiments, absorbent core 44 is physically secured to tissue 40 or extensible layer 42. FIG. 2 shows adhesive 69 securing absorbent core 44 to first inner surface 52 of extensible layer 42. A single line of adhesive 69 can be applied along the center of extensible layer 42 perpendicular to the primary direction of extensibility. Therefore, in embodiments where absorbent article 8 is extensible in cross direction "C", line of adhesive 69 is applied in longitudinal direction "L". Likewise, in embodiments where absorbent article 8 is extensible in longitudinal direction "L", line of adhesive 69 can be applied in cross direction "C" at crotch portion 18, or other portions of the absorbent article. In this manner, the movement of absorbent core 44 is restricted without stressing the absorbent core during extension of absorbent article 8.

In other embodiments, line of adhesive 69 can be applied to absorbent core 44 at a center line in contact with first surface 48 of tissue 40. Once again, line of adhesive 69 restricts movement of absorbent core 44 without stressing the absorbent core during extension of absorbent article 8.

FIG. 2 also illustrates surge layer 72 having an inner surface 74 and an outer surface 76. Surface 74 is disposed in surface-to-surface relationship with surface 50 of tissue 40. Generally, no adhesive is applied between bodyside liner 24 and absorbent pad 38. To the extent accommodated within the space defined between outer cover 26 and bodyside liner 24, the bodyside liner 24 generally has relatively free mobility with respect to absorbent pad 38.

A line of adhesive 78 can be disposed in the longitudinal direction "L" extending along e.g. the center of bodyside liner 24. Adhesive 78 thus secures bodyside liner 24 to surface 76 of surge layer 72 along a longitudinal centerline, thereby securing surge layer 72 at a proper location to bodyside liner 24 for use in absorbent article 8. Where surge layer 72 is relatively non-extensible, the longitudinal line of adhesive provides suitable securement between bodyside liner 24 and surge layer 72 while giving the bodyside liner freedom to extend outwardly in the cross-direction "C" without significant resistance from surge layer 72, whereby the integrity of the surge layer is typically not threatened by such extension.

The above described line of adhesive 78 between bodyside liner 24 and surge layer 72 preferably comprises a hot melt adhesive extending along the center of surge layer 72. Thus surge layer 72 can be secured to bodyside liner 24 while providing for relatively free movement of absorbent pad 38 with respect to the surge layer. Similarly, a line of adhesive 78A may be placed between surge layer 72 and tissue layer 40.

Fastening tabs 20, 22 can comprise hook fasteners for securing rear portion 14 of absorbent article 8 to looped material at front portion 10. Other well known securing elements can be used to support absorbent article 8 on the user. For example, a cohesive system, an adhesive fastener system, or the like may be utilized as securing elements, with suitable cooperating elements on front portion 10, as necessary, to support absorbent article 8 on the wearer. One example of a fastening tab is shown in U.S. patent application Ser. No. 421,640 filed Apr. 13, 1995 by Zehner et al, titled "Multi-Attachment Fastening System" the disclosure of which is hereby incorporated by reference in its entirety, to the extent such disclosure is consistent (not contradictory) with the subject matter disclosed herein.

Fastening tabs 20, 22 can be permanently secured to rear portion 14 of absorbent article 8 by, for example, ultrasonic bonding, adhesives, stitching, or other conventional and known methods of securement.

Figure 4:
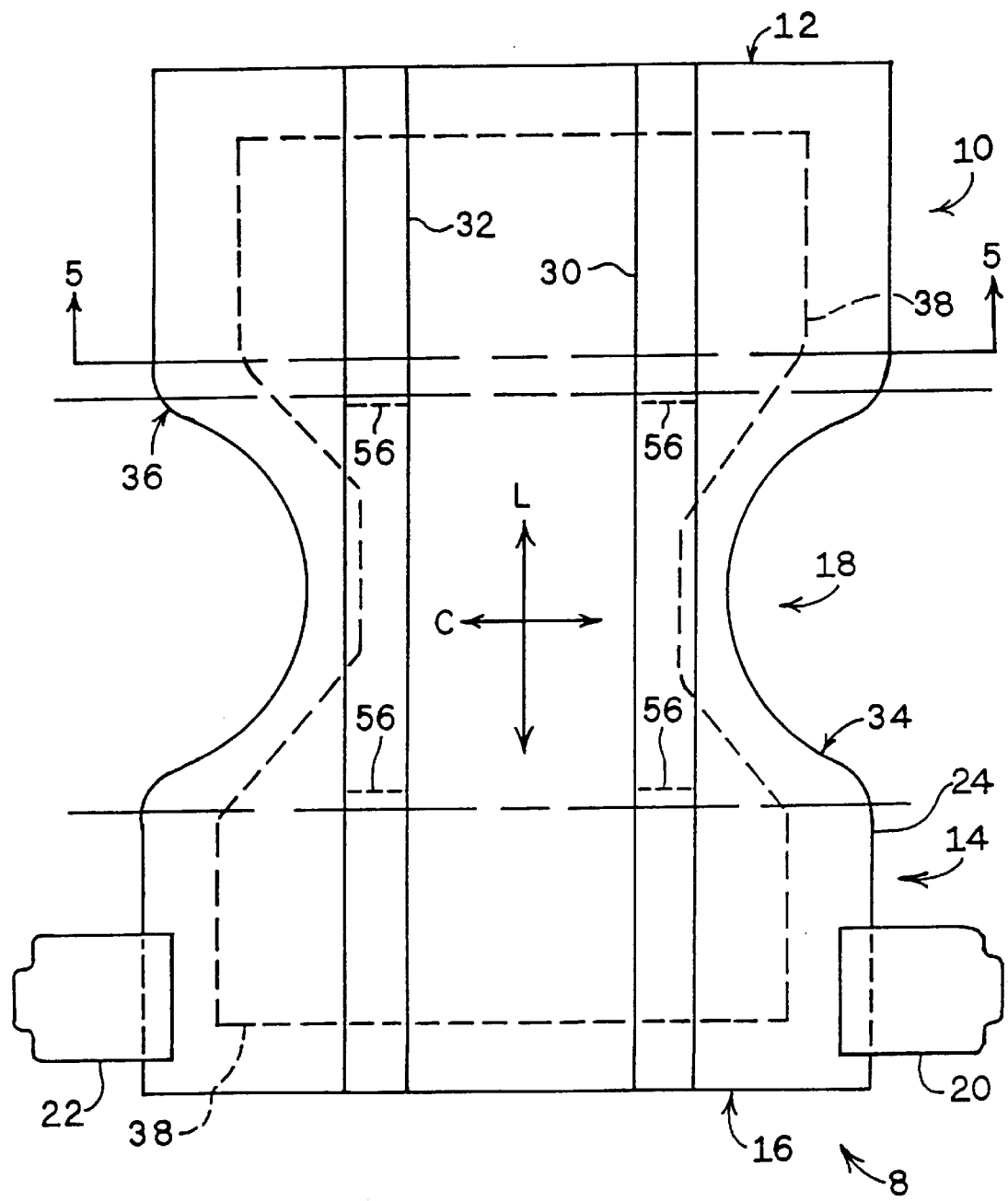
FIG. 4 shows a top view of a second embodiment having no leg elastics and wherein the tissue has been replaced by an extensible layer.

As representatively shown in FIGS. 1 and 4, bodyside liner 24 and outer cover 26 generally are coextensive and have length and width dimensions larger than the dimensions of absorbent pad 38. Thus bodyside liner 24 is generally superimposed over the entirety of the surface of outer cover 26, whereby the outer cover and the bodyside liner, in combination, define the outer perimeter of absorbent article 8. Absorbent pad 38 is preferably disposed between outer cover 26 and bodyside liner 24 inboard of the outer perimeter of absorbent article 8.

Skin-facing surface 58 of bodyside liner 24 is compliant, soft-feeling, and non-irritating to the wearer's skin. Further, bodyside liner 24 must be sufficiently porous to be permeable to aqueous-based liquids, permitting such liquids to penetrate and pass through its thickness.

A suitable bodyside liner 24 may be manufactured from a wide selection of web materials, such as porous foams, reticulated foams, apertured plastic films, woven and/or nonwoven natural fibers, synthetic fibers, or a combination of natural and synthetic fibers. Bodyside liner 24 is typically employed to help isolate the wearer's skin from liquids held in absorbent pad 38. Various woven and nonwoven fabrics can be used for bodyside liner 24. For example, bodyside liner 24 may be composed of a meltblown or spunbonded web of polyolefin fibers. Bodyside liner 24 may also be a bonded-carded-web composed of natural and/or synthetic fibers.

Bodyside liner 24 may be composed of a substantially hydrophobic and thus substantially nonwettable material, with such material optionally being treated with a surfactant or otherwise processed to impart a desired level of wettability and hydrophilicity.

In a preferred embodiment of the invention, bodyside liner 24 has substantial extensibility, which may be resilient extensibility, in at least one direction. "Resiliently extensible" can be defined as a material that is retractable to substantially its original length or width upon release of an extending force.

Bodyside liner 24 can be a nonwoven, spunbonded polypropylene fabric. See U.S. Pat. No. 5,226,992 to Morman et al, hereby incorporated by reference in its entirety, to the extent it is consistent with the disclosure herein, for teaching various materials which can be used in forming bodyside liner 24. The materials of bodyside liner 24 can be creped or necked so as to be extensible in at least one, or both, of the "L" and "C" directions (in the longitudinal direction "L" and/or the cross direction "C").

Bodyside liner 24 may comprise a multiplicity of components, layers, or partial layers, which correspond to any of the materials disclosed herein, as well as others known in the art. Materials of bodyside liner 24 can be treated with a selected amount of surfactant, such as about 0.28% by weight Trition X-102 surfactant available from Rohm and Haas Corp. of Philadelphia, Pa. The surfactant can be applied by any conventional means such as spraying, printing, brush coating or the like.

In yet another embodiment of the present invention, bodyside liner 24 can comprise a stretch-bonded laminate having appropriate elasticity and width to create overall surface contact between absorbent article 8 and the body of a wearer. A stretch-bonded laminate comprises at least a two-layered composite in which one layer is a gatherable layer and the other layer a stretchable layer. The layers are joined together when the stretchable layer is in a stretched condition so that, upon relaxing the composite of the joined layers, the gatherable layer is gathered. The stretchable layer can be a film of stretchable material, such as a layer of styrene ethylene butylene block copolymer or other elastomeric polymer, or a plurality of optionally spaced strands of a stretchable material such as latex, LYCRA®, or the like. Other materials with similar properties may also be provided integral with or attached to bodyside liner 24. Such materials should not interfere with the soft texture of bodyside liner 24 against the skin of a user.

Bodyside liner 24 can have an extensibility of at least about 30%, preferably at least about 100%, more preferably at least about 200%, in the cross-direction "C". In some embodiments, bodyside liner 24 additionally can have similar extensibility in longitudinal direction "L". In other embodiments, bodyside liner 24 can be extensible only in longitudinal direction "L".

In some embodiments, bodyside liner 24 can have some retractability such that, when forces on outer cover 26 are released, the bodyside liner can at least partially retract toward its original position. Retraction of bodyside liner 24 can avoid bunching or unevenness of the bodyside liner of personal care article 8 when outer cover 26 returns to substantially its original position.

Outer cover 26 preferably comprises a material extending over and about substantially the entirety of the overall area of the absorbent article 8, and capable of being extended in at least the cross-direction "C". Such materials include knitted and loosely woven fabrics, or nonwoven fabrics such as bonded carded webs, spunbonded webs and meltblown webs. A meltblown web typically includes meltblown microfibers. The material may also have multiple layers such as, for example, multiple spunbonded layers and/or multiple meltblown layers. The material may be made of polymers such as, for example, polyolefins. Exemplary polyolefins include polypropylene, polyethylene, ethylene copolymers and propylene copolymers, including ethylene propylene copolymer. See U.S. Pat. No. 5,226,992 to Morman et al. incorporated by reference earlier, for teaching various materials which can be used to form outer cover 26. A preferred material for the outer cover 26 can comprise an extensible film laminated to a necked nonwoven spunbonded material.

Alternative constructions of outer cover 26 may include a woven or non-woven fibrous web layer which has been totally or partially constructed or treated to impart desired levels of liquid impermeability to selected regions thereof, such as regions that are adjacent or proximate absorbent pad 38. Optionally, in some embodiments, an additional outer layer (not shown) may overlie outer cover 26.

Outer cover 26 may optionally be composed of microporous, breathable material that permits vapors to escape from the absorbent article while preventing liquid exudates from passing through. An exemplary suitable microporous film is a material known as PMP-1, which is available from Mitsui Toatsu Chemicals, Inc. a company having offices in Tokyo, Japan; or a polyolefin film known as XKO-8044 and available from 3M Company of Minneapolis, Minn.

In another embodiment of the invention, outer cover 26 can be a nonwoven, spunbond polypropylene layer. Such layer can be creped or necked so as to be extensible in at least one of the "L" and "C" directions or in both the longitudinal direction "L" and the cross direction "C". Outer cover 26 can have an extensibility of at least about 30%, preferably at least about 100%, and more preferably at least about 200% in the cross-direction "C". In some embodiments, outer cover 26 has similar extensibility in longitudinal direction "L".

Other materials having other advantageous characteristics are also useful as outer cover 26. For example, outer cover 26 can comprise a stretch-bonded laminate. Methods of making such materials are known to those skilled in the art.

Preferably both bodyside liner 24 and outer cover 26 are extensible. Such extensibility preferably enables both layers to be extended in the same direction. At least one of bodyside liner 24 and outer cover 26 preferably is resiliently extensible, i.e. retractable to substantially its original length and/or width upon release of the extending force. For example, in a preferred embodiment of absorbent article 8, after a longitudinal elongation of 200% to outer cover 26, whereupon the length in the "L" direction is 3 times the previously unstretched length, outer cover 26 can return to 150% of its original length thus retracting 75% of the stretch amount. Thus, as used herein, a material which can recover at least about 75% of a stretch amount is resiliently extensible.

In preferred embodiments, when absorbent article 8 is stretched, at least one of bodyside liner 24 and outer cover 26 possess sufficient retraction properties to return the absorbent article to substantially its original pre-stretch size and shape upon release of fastening tabs 20, 22 or other such restraints. In such instance, the element that is extensible, without being itself resiliently extensible, can follow the retracting liner/cover to the retracted size upon release. In other embodiments, both bodyside liner 24 and outer cover 26 can be resiliently extensible, and thus, upon release of fastening tabs 20, 22, can and do assist each other in returning absorbent article 8 to a retracted condition which may be substantially the earlier relaxed size and shape. In such an arrangement, bodyside liner 24 and outer cover 26 can have substantially equal retractibility in each direction.

In some embodiments where bodyside liner 24, outer cover 26, and extensible layer 42 are all extensible in at least the cross-direction, the extensible layer enables the outer cover to extend at least about 30 percent in the cross-direction without damaging absorbent pad 38. In other embodiments, outer cover 26 can extend at least about 200 percent in the cross-direction (as well as extensible layer 42) without damaging absorbent pad 38.

In other embodiments, where bodyside liner 24, outer cover 26, and extensible layer 42 are all extensible in at least the longitudinal direction, the extensible layer enables the outer cover to extend at least about 30 percent in the longitudinal direction without damaging absorbent pad 38. In other embodiments, outer cover 26, as well as extensible layer 42, can extend at least about 100 percent in the longitudinal direction without damaging absorbent pad 38.

In many embodiments, it is preferred that extensible layer 42 have a lower or equal stress/strain ratio than the stress/strain ratio of outer cover 26. In such an arrangement, extensible layer 42 extends at least as far as outer cover 26 under similar force, to ensure no tearing or breaking of the extensible layer can occur.

Leg elastics 28 may be formed from separate materials which are attached to outer cover 26 and/or bodyside liner 24. Materials suitable for forming the leg elastics include LYCRA® strands, ribbons, or one or more layers of a polymeric and/or elastomeric material that may be adhered, while in a stretched or extended position, to absorbent article 8, thus forming leg elastics 28. Leg elastics 28 accommodate limited extensibility of the absorbent article in longitudinal direction "L", from and to a relaxed condition. Alternatively, the material forming leg elastic 28 can be attached, in a relaxed condition, to absorbent article 8 while the article is pleated, such that elastic retractive forces are imparted to at least crotch portion 18 of absorbent article 8 when the leg elastic is elongated along the length of the absorbent article.

In the embodiment of FIG. 4, outer cover 26 and/or bodyside liner 24 are formed from materials at least stretchable in longitudinal direction "L", whereby extensible leg elastics 28 need not be provided for such embodiments of absorbent article 8.

Still referring to FIG. 4, opposing left and right spaced containment flaps 30, 32 extend longitudinally along the length of absorbent article 8 inwardly of respective side edges 34, 36. In such embodiments, containment flaps 30, 32 are typically secured to bodyside liner 24. Dashed lines 56 indicate the longitudinally-inboard extremities of where the entire surfaces of the containment flaps which are facing bodyside liner 24 are secured to the bodyside liner outwardly from crotch portion 18. Thus, outwardly from dashed lines 56 in front portion 10 or rear portion 14 of absorbent article 8, containment flaps 30, 32 generally cannot open outwardly away from bodyside liner 24. However, inwardly of edges 12, 16 from dashed lines 56, containment flaps 30, 32 are secured to bodyside liner 24 only at the edges thereof closest to bodyside liner 24. Thus the upward edge can open and the containment flaps can unfold, to thus stand up and receive and restrain exudates.

Exemplary containment flaps are set forth in U.S. Pat. No. 4,704,116 issued Nov. 3, 1987 to K. Enloe, the disclosure of which is hereby incorporated by reference in its entirety to the extent that it is consistent (not contradictory) herewith.

Waist elastics (not shown) can extend generally about the waist of absorbent article 8. Front waist elastics and rear waist elastics (not shown) generally comprise strands, ribbons or one or more layers of a polymeric and/or other elastomeric material. Such elastic material can be adhered or otherwise mounted in absorbent article 8 while the elastic is in a stretched condition. Waist elastics can comprise one or more individual strands of elastomeric material, preferably in a spatially separated, generally parallel arrangement.

In some of the embodiments which comprise extensible outer covers 26 and/or extensible bodyside liners 24, waist elastic elements can be omitted. Such absorbent articles 8 are devoid of such separate waist elastic elements. Extensible bodyside liner 24 and/or extensible outer cover 26 can thus obviate the need for separate waist elastic elements while retaining the appropriate stretch function of the waist sections.

Absorbent pad 38 may be manufactured in a wide variety of sizes and shapes (for example, rectangular, trapezoidal, T-shape, I-shape, hourglass shape, etc.) and from a wide variety of materials. The size, and absorbent capacity, of absorbent pad 38 should be compatible with the size of the intended wearer and the anticipated liquid loading imparted by the intended use of the absorbent pad.

Absorbent pad 38 contains absorbent core 44 preferably enveloped by tissue 40 and extensible layer 42. Adhesive 46 preferably comprises cold adhesive applied to tissue 40 and/or extensible layer 42 about at least the outer perimeter of tissue 40 and layer 42, outwardly of absorbent core 44. Other known adhesives or bonding techniques may be utilized in place of cold adhesive to secure surface 48 of tissue 40 to surface 52 of extensible layer 42.

Referring specifically to FIGS. 1 and 2. tissue 40 typically comprises a single-ply, low porosity creped wadding or the like. Other tissues can also function as tissue 40 provided the proper porosity and other characteristics are present. An exemplary tissue has a basis weight of 20 grams per square meter and a porosity of approximately 100 cubic feet per minute per foot squared.

For the purposes of the present invention, the porosity value of any of the components can be determined by ASTM Method D 737-75 "Standard Test Method for Air Permeability of Textile Fabrics", dated Jun. 30, 1975 (reapproved 1980). The method is conducted on a single sheet of sample material. A permeability testing apparatus of the type suitable for use with this method is a high pressure differential air permeability machine, such as available from Frazier Precision Instrument Company located in Gaithersburg, Md.

Extensible layer 42 can comprise a spunbond material. Necked, stretched spunbond, is particularly useful. An exemplary material comprises thermally point bonded, polypropylene spunbond having a basis weight of about 12 to about 36 grams per square meter. Such material is stretched about 5% to about 25% lengthwise (machine direction) with appropriate heating, reducing the width (cross machine direction dimension) by about 30% to about 60%. The resulting extensible layer 42 is extensible in cross direction "C" and has modest elastic retraction. U.S. Pat. No. 4,965,122 to Morman describing such neck stretched spunbond webs, is hereby incorporated by reference to the extent the disclosure is consistent (not contradictory) with the information disclosed herein.

Other materials suitable for use as extensible layer 42 can include neck bonded laminates, stretch bonded laminates, carded webs, and polymers, such as, for example, polyolefins. The materials described earlier with respect to outer cover 26 can be utilized for extensible layer 42. Extensible layer 42 may be made from other materials not specifically disclosed here but having suitable characteristics consistent with the properties of the materials which have been specifically described.

Extensible layer 42 preferably has substantially the same or a lower stress/strain ratio, in each direction, as outer cover 26. Therefore, during use, extensible layer 42 tends to extend substantially at least the same distance as outer cover 26 due to forces extending the layer. Of course, undue loading that could destroy the function of outer cover 26 and/or extensible layer 42 during use is not contemplated by the invention.

Dry strength and wet strength of extensible layer 42 are sufficient for the layer to withstand the manufacturing process placing the layer on absorbent article 8, and to withstand normal use of the finished product (absorbent article 8) on the body of a wearer.

While extensible layer 42 is disclosed as a single layer of material, extensible layer 42 can comprise a plurality of layers (not shown), where at least one of the plurality of layers is made from the materials disclosed earlier for the extensible layer.

Absorbent core 44 suitably comprises a matrix of hydrophilic fibers, such as a web of cellulosic fluff, preferably in combination with a high-absorbency material commonly known as superabsorbent material. In a preferred embodiment, absorbent core 44 comprises a mixture of superabsorbent hydrogel-forming material and wood pulp fluff. In place of the wood pulp fluff, one may use synthetic, polymeric, meltblown fibers or a combination of meltblown fibers and natural fibers. The superabsorbent material may be substantially homogeneously mixed with the hydrophilic fibers or may be otherwise combined into the absorbent core.

Alternatively, absorbent core 44 may comprise a laminate of fibrous webs and superabsorbent material or other suitable means of maintaining a superabsorbent material in a localized area.

The high-absorbency material in absorbent core 44 can be selected from natural, synthetic and modified natural polymers and materials. The high absorbency materials can be inorganic materials, such as silica gels, or organic compounds, such as cross-linked polymers. The term cross-linked refers to any means for effectively rendering normally water-soluble materials substantially water insoluble but swellable, whereby absorbent properties are available but the swelled material is substantially immobile after absorbing water-based liquids. Such means can include, for example, physical entanglement, crystalline domains, covalent bonds, ionic complexes and associations, hydrophilic associations such as hydrogen bonding, and hydrophobic associations or Van der Waals forces.

Bodyside liner 24 is secured to outer cover 26 about and outwardly of at least an outer perimeter of absorbent pad 38. Typically, such securement is provided by pattern of adhesive 66. The pattern can comprise swirls of adhesive 66 shown in FIG. 3. The swirls of adhesive 66 correspond to the twelve spaced spray guns 68 of adhesive applicator 70 aligned across the width of outer cover 26. Such an adhesive pattern decreases the amount of adhesive 66 required to adhere and maintain surface 64 of outer cover 26 to extensible layer 42 and the perimeter of surface 60 of bodyside liner 24.

In other embodiments, pattern of adhesive 66 can comprise overlapping swirls of adhesive applied to surface 64 of outer cover 26. Such an embodiment would be similar to the illustration of FIG. 3 except adjacent swirls of adhesive 66 would overlap or touch each other. In other embodiments, pattern of adhesive 66 can comprise an array of spaced lines of adhesive extending in longitudinal direction "L". Such an embodiment would include, for example, twelve lines substantially equidistantly spaced from adjacent lines and extending the length of outer cover 26 in longitudinal direction "L".

The swirling patterns of adhesive 66 shown in FIG. 3 secure outer cover 26 to extensible layer 42 while having open adhesive-free spaces 67 devoid of adhesive such that outer cover 26, comprising a resiliently extensible element, can stretch in at least one direction.

Extensible layer 42 is generally extensible in the same direction as outer cover 26. Pattern of adhesive 66 generally does not significantly prevent extensible layer 42 and outer cover 26 from extending in at least one direction. The direction of extension preferably is cross direction "C". The open adhesive-free spaces 67 increase the extensibility of a substrate formed by outer cover 26, extensible layer 42, absorbent core 44. and bodyside liner 24. The greater the surface area of adhesive-free spaces 67, the less securement there is of outer cover 26 to extensible layer 42. The less securement that is present herein, the greater than amount of stretchability that is available to the substrate. Likewise, the greater the surface that is joined by adhesives 66, the less amount of stretch from outer cover 26 and extensible layer 42 that is available for use of the device.

In some embodiments, outer cover 26 and extensible layer 42 can both extend in longitudinal direction "L" or in both the longitudinal and cross directions. Extension in both directions is possible where extensible adhesives are utilized as adhesive 66. One such extensible or elastic adhesive particularly useful as adhesive 66 is known as H2525A, available from AtoFindley Adhesives, Inc. of Wauwatosa, Wis. Such elastic adhesive can be applied in a pattern that covers a high fraction of the interface between first surface 52 of extensible layer 42 and first surface 52 of outer cover 26. Even at 100% coverage of the interface, extensibility of extensible layer 42 and outer cover 26 is not inhibited when the elastic adhesive is sufficiently extensible.

While elastic adhesive is disclosed for use as adhesive 66 joining outer cover 26 and extensible layer 42, such elastic adhesive can be utilized as a replacement for any other type of adhesive disclosed for any other location in the application. For example, line of adhesive 78 can comprise an elastic adhesive.

Less extensible adhesives have the potential to prevent extensibility of extensible layer 42 and outer cover 26, if not properly applied. Thus, where bodyside liner 24 and outer cover 26 are extensible in both cross direction "C" and longitudinal direction "L", and adhesive 66 is not elastic, the adhesive must comprise patterns not including solid lines of adhesive in the longitudinal direction. For example, patterns of adhesive 66 can be at various angles with respect to the pattern of FIG. 3 showing longitudinal spaced unconnected areas of adhesive. Such patterns prevent or limit adhesive 66 from "locking up" stretch of outer cover 26 in longitudinal direction "L" or cross direction "C". As used herein, "locking up" means an adhesive or glue preventing an extensible element from extending the amount designed because of the adhesive creating a bond at at least a surface of the extensible material. Likewise, selected spray guns 68 of adhesive applicator 70 can be intermittently or continuously deactivated to intermittently vary the regions of second inner surface 64 which receives the adhesive pattern and/or to vary the density of the adhesive pattern. Such intermittent application of adhesive 66 can permit outer cover 26 to remain extensible in the longitudinal direction. Surge layer 72 generally is located between tissue 40 and bodyside liner 24. Surge layer 72 assists in spreading exudates over a substantial portion of absorbent pad 38. Thus, surge layer 72 assists absorbent pad 38 in absorbing a sudden large amount of urine or other body exudates. Surface 74 of surge layer 72 is in surface-to-surface contact with surface 50 of tissue 40 and surface 76 of the surge layer is in surface-to-surface contact with surface 60 of bodyside liner 24.

Surge layer 72 can comprise materials set forth in U.S. Pat. No. 5,486,166 issued Jan. 23, 1996 to C. Ellis and D. Bishop, entitled, "Fibrous Nonwoven Web Surge Layer for Personal Care Absorbent Articles and the Like"; and U.S. Pat. No. 5,490,846 issued Feb. 13. 1996 to C. Ellis and R. Everett, entitled, "Improved Surge Management Fibrous Nonwoven Web for Personal Care Absorbent Articles and the Like": the disclosures of which are herein incorporated by reference to the extent the disclosures are consistent (not contradictory) with the information disclosed herein. Further, other surge layer materials known in the art can also be utilized.

Optionally, a second line of adhesive (not shown) extending in the longitudinal direction "L" can be located between surge layer 72 and absorbent pad 38. Such a line of adhesive assists in preventing absorbent pad 38 from shifting laterally a significant distance, while permitting bodyside liner 24 to extend, at least in the cross-direction "C". a desired distance. Such an arrangement assists in ensuring that absorbent pad 38 remains centered in absorbent article 8.

Such a second line of adhesive can also comprise a broken line of adhesive (not shown) disposed at spaced intervals along a length of bodyside liner 24 parallel to longitudinal direction "L". Such a broken line can be formed by intermittent actuation of spray guns 68 applying pattern of adhesive 66. Thus, for embodiments wherein both bodyside liner 24 and outer cover 26 are extensible in the cross-direction "C" and in the longitudinal direction "L", the broken line of adhesive will not significantly lock up, or prevent extension of the bodyside liner in the longitudinal direction.

Manufacturing absorbent article 8 can include applying bodyside liner 24 to surface 50 of tissue 40 such that the bodyside liner overlies, and extends outwardly of, absorbent pad 38. Thus bodyside liner 24 overlies and contacts portions of outer cover 26 that extend outwardly of absorbent pad 38 as illustrated in FIG. 2. Patterns of adhesive 66 thus secure outer perimeter of outer cover 26 to bodyside liner 24 at locations disposed outwardly of the outer perimeter of absorbent pad 38.

Absorbent article 8 as shown in FIGS. 1 and 2 illustrates the relatively free mobility of bodyside liner 24 and outer cover 26 relative to absorbent core 44. Such mobility is present especially when optional line of adhesive 69 is not used to secure portions of absorbent core 44 to extensible layer 42. Thus, the embodiment of FIGS. 1 and 2 enables bodyside liner 24 and outer cover 26 to be extensible, preferably resiliently extensible, along with extensible layer 42, such that extensible layer 42 does not tear or break, and thus does not release superabsorbent or other absorbent material from absorbent pad 38.

Figure 5:
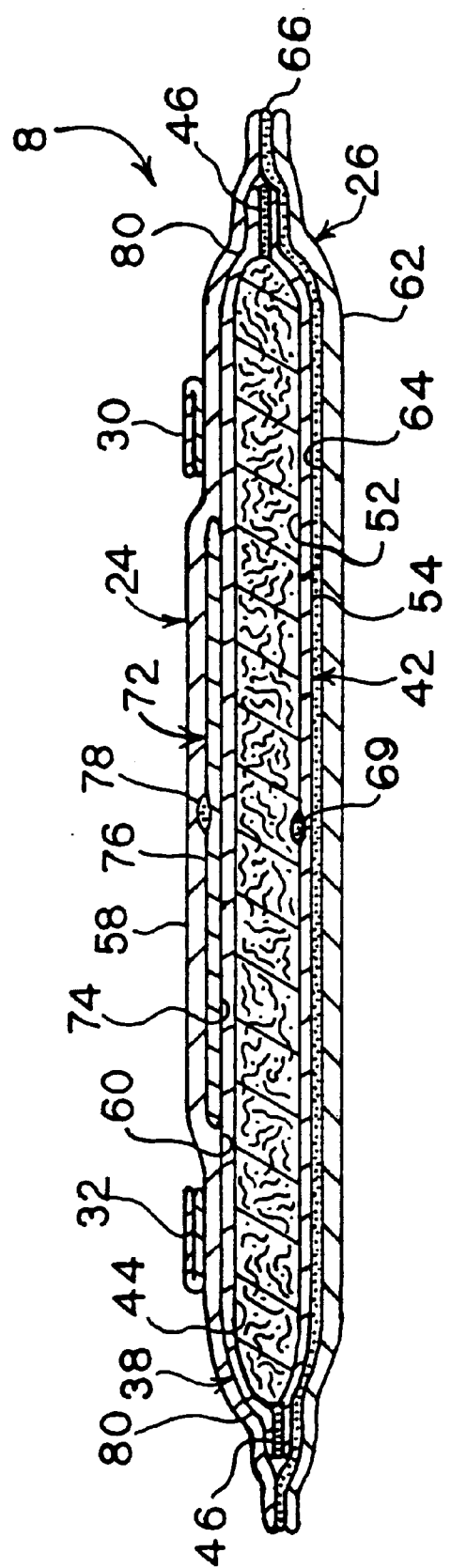
FIG. 5 shows a cross section view of the absorbent article taken at 5—5 of FIG. 4.

The second embodiment of the invention shown in FIG. 4 is further illustrated in the cross-section of FIG. 5. The embodiment of FIG. 5 is substantially identical to the embodiment of FIG. 2 except tissue 40 has been replaced by a layer 80 of other material. Layer 80 of material can comprise, for example, a layer or layers of materials such as the materials described for extensible layer 42.

Layer 80 preferably comprises an extensible layer that is extensible in at least the same direction or directions as bodyside liner 24, extensible layer 42, and outer cover 26. Thus, when absorbent article 8 is applied to the body of a wearer, the relative free mobility of layers 42, 80 with respect to absorbent core 44 enables layers 42, 80 to extend with bodyside liner 24 and outer cover 26 without tearing or other damage to absorbent core 44. Bodyside liner 24 and outer cover 26 preferably have greater or equal stress/strain ratios than extensible layers 42, 80 in longitudinal direction "L" and cross-direction "C" so that no one element provides the majority of the resistance, or otherwise controls the resistance, to forces extending absorbent article 8 during application and usage. Such shared resistance decreases the likelihood of failure tearing or breakage of extensible layers 42, 80 and subsequent leakage of superabsorbent particles and absorbent material from absorbent pad 38.

Absorbent pad 38 includes extensible layers 42, 80 that can extend as needed. Absorbent core 44 remains between extensible layers 42, 80 and due to the extensibility of layers 42, 80 and the fact that layers 42, 80 are not bonded to the absorbent core, the absorbent core is not significantly stretched, and thus is not damaged, when absorbent article 8 is stretched. Thus, extensible layers 42, 80 have essentially full freedom of movement with respect to absorbent core 44, to move within absorbent article 8, in reaction to extension of bodyside liner 24 and outer cover 26.

The modifications and alternatives set forth in the embodiment of FIGS. 1 and 2 generally can be utilized with the embodiment of FIGS. 4 and 5. However, tissue 40 is replaced by layer 80.

Those skilled in the art will now see that certain modifications can be made to the invention herein disclosed with respect to the illustrated embodiments, without departing from the spirit of the instant invention. And while the invention has been described above with respect to the preferred embodiments, it will be understood that the invention is adapted to numerous rearrangements, modifications, and alterations, all such arrangements, modifications, and alterations are intended to be within the scope of the appended claims.

To the extent the following claims use means plus function language, it is not meant to include there, or in the instant specification, anything not structurally equivalent to what is shown in the embodiments disclosed in the specification.

Having thus described the invention, what is claimed is:

1. An absorbent article including a rear portion, a front portion, and a crotch portion connecting said rear portion and said front portion, said absorbent article having a cross direction extending across said absorbent article and a longitudinal direction extending through the front, crotch, and rear portions, said absorbent article comprising:

(a) an absorbent core having a first side and a second side and an outer perimeter;

(b) an extensible layer of material having a first surface and an opposing second surface, the first surface of said extensible layer being disposed adjacent the first side of said absorbent core;

(c) an extensible outer cover having a third outer cover surface and a fourth opposing outer cover surface, the second surface of said extensible layer being disposed in surface-to-surface relationship with the third outer cover surface; and (d) a pattern of adhesive disposed between said extensible layer and said outer cover, the pattern of adhesive mounting said extensible layer to said outer cover such that extension of said outer cover extends said extensible layer, said extensible layer having the ability to extend in response to extension of said outer cover while at least a portion of the absorbent core is free to move within the absorbent article, with respect to the outer cover without significant loading of said absorbent core.

2. An absorbent article as in claim 1 wherein said extensible layer comprises a layer of extensible spunbond material.

3. An absorbent article as in claim 1, said outer cover comprising a neck bonded laminate.

4. An absorbent article as in claim 1, said absorbent article including first and second containment flaps.

5. An absorbent article as in claim 1, said absorbent article being devoid of separate waist elastic elements, and being resiliently stretchable in the waist.

6. An absorbent article as in claim 1, said absorbent article including leg elastics disposed at least in the crotch portion of said absorbent article, said leg elastics providing extensibility and retraction in the longitudinal direction.

7. An absorbent article as in claim 1, said pattern of adhesive comprising a plurality of swirl patterns.

8. An absorbent article as in claim 1, including a second layer of material having a fifth surface and an opposing sixth surface, the fifth surface of said second layer being disposed adjacent the second side of said absorbent core, said extensible layer and said second layer containing said absorbent core, and wherein said absorbent core, said extensible layer, and said second layer, in combination, comprise an absorbent pad.

9. An absorbent article as in claim 8, said extensible layer and said second layer being secured to each other about at least a portion of an outer perimeter of said absorbent core.

10. An absorbent article as in claim 8, including a bodyside liner having a seventh surface and an opposing eighth surface, the seventh surface of said bodyside liner being disposed in surface-to-surface relationship with the sixth surface of said second layer.

11. An absorbent article as in claim 8 including a bodyside liner on an opposite side of said absorbent core from said outer cover, and wherein at least one of said bodyside liner and said outer cover comprise a resiliently extensible material.

12. An absorbent article as in claim 8 including a bodyside liner on an opposite side of said absorbent core from said outer cover, and said bodyside liner and said outer cover both being resiliently extensible, and having substantially equal resilient extensibility in each direction.

13. An absorbent article as in claim 8 including a bodyside liner on an opposite side of said absorbent core from said outer cover, and said bodyside liner and said outer cover both being extensible in at least the cross-direction.

14. An absorbent article as in claim 8 including a bodyside liner on an opposite side of said absorbent core from said outer cover, and said absorbent core, said extensible layer, and a tissue, in combination, comprising an absorbent pad, said absorbent pad having an outer perimeter, said pattern of adhesive being disposed on the third surface of said outer cover outwardly of said absorbent pad such that said outwardly disposed adhesive secures said outer cover to said bodyside liner at locations disposed outwardly of the outer perimeter of said absorbent pad.

15. An absorbent article including a rear portion, a front portion, and a crotch portion connecting said rear portion and said front portion, said absorbent article having a cross direction extending across said absorbent article and a longitudinal direction extending through the front, crotch, and rear portions, said absorbent article comprising:

(a) an extensible outer cover having a first inner surface and an opposing second outer surface;

(b) a bodyside liner having a third body contacting surface and an opposing fourth surface, the fourth surface of said bodyside liner being mounted in surface-to-surface relationship to at least a portion of the first inner surface of said outer cover;

(c) an absorbent pad disposed between said bodyside liner and said outer cover, said absorbent pad comprising an absorbent core having a first side and an opposing second side, said absorbent pad including a first extensible layer of material disposed between the first side of said absorbent core and said outer cover, said first extensible layer having a first surface and an opposing second surface, a portion less than the entirety of the first surface of said first extensible layer being secured to the first inner surface of said outer cover such that said extensible layer and said outer cover layer can expand with differential stretching without damaging said extensible layer, and a second layer of material disposed between the second surface of said absorbent core and said bodyside liner; and (d) adhesive material disposed between said outer cover and said first extensible layer and mounting said outer cover and said first extensible layer to each other, such that extension of said outer cover extends said extensible layer within said absorbent article without significant loading of said absorbent core.

16. An absorbent article as in claim 15 wherein said outer cover comprises a resiliently extensible material.

17. An absorbent article as in claim 15 wherein said outer cover comprises a neck bonded laminate.

18. An absorbent article as in claim 15 wherein said bodyside liner comprises an extensible material.

19. An absorbent article as in claim 18 wherein said bodyside liner, said outer cover, and said first extensible layer are extensible in at least the cross-direction, said first extensible layer enabling said outer cover to extend at least about 30 percent in the cross-direction without damaging said absorbent pad.

20. An absorbent article as in claim 18 wherein said first extensible layer enables said outer cover to extend at least about 200 percent in the cross-direction without damaging said absorbent pad.

21. An absorbent article as in claim 20 wherein said first extensible layer enables said outer cover to extend at least about 30 percent in the longitudinal direction without damaging said absorbent pad.

22. An absorbent article as in claim 15 wherein the adhesive material disposed between said outer cover and said first extensible layer comprises elastic adhesive material.

23. An absorbent article as in claim 15, said second layer comprising a tissue.

24. An absorbent article as in claim 23, said tissue and said first extensible layer being secured to each other about said absorbent core, such that said absorbent core is enclosed by the combination of said tissue and said first extensible layer, in combination with said absorbent core, to thereby comprise said absorbent pad.

25. An absorbent article as in claim 15, said absorbent pad having an outer perimeter, said adhesive material extending outwardly beyond the outer perimeter such that said adhesive material secures said outer cover to said bodyside liner.

26. An absorbent article as in clam 15, said second layer comprising a spunbond material.

27. An absorbent article as in claim 15, said second layer comprising an extensible material.

28. An absorbent article as in claim 27, said second layer being an extensible layer, said first extensible layer and said second extensible layer being secured to each other about said absorbent core, such that said absorbent core is enclosed by the combination of said first extensible layer and said second extensible layer to thereby form said absorbent pad.

29. An absorbent article as in claim 27, said second layer being an extensible layer, said extensible layer and said second extensible layer having substantially equal extensibility in at least the cross-direction.

30. An absorbent article as in claim 15, said outer cover having a greater or equal stress/strain ratio than said extensible layer.

31. An absorbent article including a rear portion, a front portion, and a crotch portion connecting said rear portion and said front portion, said absorbent article having a cross direction extending across said absorbent article and a longitudinal direction extending through the front, crotch, and rear portions, said absorbent article comprising:

(a) an absorbent core having a first side and a second side:

(b) a layer of material having a first surface and an opposing second surface, the first surface of said layer being disposed adjacent the first side of said absorbent core;

(c) an extensible outer cover having a third outer cover surface and a fourth opposing outer cover surface, the second surface of said layer being disposed in surface-to-surface relationship with the third outer cover surface; and (d) elastic adhesive disposed between said layer and said outer cover, said elastic adhesive mounting said layer to said outer cover such that extension of said outer cover can extend said adhesive without significant loading of said absorbent core.

32. An absorbent article as in claim 31, said layer comprising an extensible layer.

* * * * *

UNITED STATES PATENT AND TRADEMARK OFFICE
CERTIFICATE OF CORRECTION

PATENT NO. : 6,129,720  
DATED : October 10, 2000  
INVENTOR(S) : Timothy J. Blenke, et al.

Page 1 of 1

It is certified that error appears in the above-identified patent and that said Letters Patent is hereby corrected as shown below:

Title page,
Item [56] References Cited, delete "4,701,114 10/1987 Wilson et al" and insert -- 4,704,114 11/1987 Wilson et al. -- in place thereof.

Column 13,
Line 52, delete "(not shown)" and insert -- 78A (FIG. 2) -- in place thereof;
Line 57, after "C" delete "." and insert -- , -- in place thereof.

Signed and Sealed this

Sixteenth Day of October, 2001

*Attest:*

NICHOLAS P. GODICI
*Attesting Officer*   Acting Director of the United States Patent and Trademark Office